United States Patent [19]
Eastman

[11] Patent Number: 5,463,162
[45] Date of Patent: * Oct. 31, 1995

[54] ALKYLATION CATALYST REGENERATION

[75] Inventor: Alan D. Eastman, Bartlesville, Okla.

[73] Assignee: Phillips Petroleum Company, Bartlesville, Okla.

[*] Notice: The portion of the term of this patent subsequent to Nov. 23, 2010, has been disclaimed.

[21] Appl. No.: 184,792

[22] Filed: Jan. 21, 1994

[51] Int. Cl.⁶ .................. C07C 2/62; C07C 7/10
[52] U.S. Cl. .............. 585/724; 585/802; 585/857
[58] Field of Search .................. 585/724, 802

[56] References Cited

U.S. PATENT DOCUMENTS

| | | | |
|---|---|---|---|
| 3,795,712 | 3/1974 | Torck et al. ............... | 260/671 |
| 4,663,026 | 5/1987 | Louie et al. ............... | 208/262 |
| 5,262,579 | 11/1993 | Child et al. ............... | 585/802 |
| 5,264,649 | 11/1993 | Eastman et al. ........... | 585/802 |
| 5,264,650 | 11/1993 | Better et al. .............. | 585/802 |

Primary Examiner—Asok Pal
Attorney, Agent, or Firm—Charles W. Stewart

[57] ABSTRACT

Disclosed is a process for removing acid soluble oils, produced as an undesirable by-product of an HF catalyzed alkylation reaction, from a fluid containing a sulfone compound. The process includes the use of hydrocarbons to remove ASO from the sulfone-containing fluid.

11 Claims, 2 Drawing Sheets

5,463,162

ALKYLATION CATALYST REGENERATION

The present invention relates to the regeneration of a catalyst composition utilized in a hydrocarbon conversion process. More particularly, the invention relates to the regeneration of a catalyst mixture, comprising a sulfone compound and a hydrogen halide compound, utilized in the alkylation of olefin hydrocarbons by isoparaffin hydrocarbons.

BACKGROUND OF THE INVENTION

It has recently been discovered that a mixture, comprising a sulfone compound and a hydrogen halide compound, is an effective catalyst for use in the alkylation of olefin hydrocarbons by isoparaffin hydrocarbons to produce an alkylate reaction product, or alkylate. The alkylate reaction product generally contains hydrocarbons having seven or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain polymeric reaction by-products such as those referred to as acid-soluble oils, or ASO. These polymeric reaction by-products are referred to as acid-soluble oils because they are soluble in the catalyst utilized in the alkylation process; and thus remain in the catalyst phase when the alkylate product resulting from the contact of a hydrocarbon mixture with an alkylation catalyst is separated from the alkylation catalyst.

In an alkylation process which continuously separates the catalyst phase from the alkylation reaction product for reuse in the process reaction zone, there is a buildup of ASO in the catalyst. Over time the ASO concentration will reach unacceptable concentration levels if not removed. A low concentration of ASO in the alkylation catalyst comprising a sulfone component and a hydrogen halide component is believed to have a beneficial effect upon the alkylation process or its product. However, higher concentrations of ASO in the alkylation catalyst have an adverse effect upon the catalyst activity and the final alkylate end-product. An ASO concentration in the alkylation catalyst that exceeds certain acceptable limits will result in lowering the octane of the alkylate end-product with incremental increases in the ASO concentration causing incremental decreases in the alkylate octane.

In conventional alkylation processes that use hydrogen fluoride (HF) as a catalyst, as opposed to the use of the aforementioned novel catalyst comprising a sulfone component and a hydrogen halide component, there are certain known methods used to remove the ASO from the HF catalyst used in a continuous alkylation process. Particularly, enough of a portion of the HF catalyst that is utilized in the alkylation process is treated, or regenerated, so as to remove an amount of ASO at a rate that approximates the rate of accumulation of ASO in the alkylation catalyst. This is done by passing a portion of the HF catalyst to a stripping vessel whereby the HF is stripped from the ASO by means of a vaporous hydrocarbon such as isobutane with the HF passing as a part of the vaporous overhead stream from the stripping vessel and the ASO passing as a bottoms stream from the stripping vessel for further processing.

While the conventional alkylation catalyst regeneration techniques have worked well in the regeneration of the conventional HF catalyst, conventional means cannot be used to regenerate an alkylation catalyst mixture which includes a sulfone component. This is because the boiling range of ASO overlaps the boiling temperatures of certain sulfones such as sulfolane. Therefore, simple distillation techniques as are used to separate HF from ASO cannot be used to effectively regenerate a sulfone-containing alkylation catalyst. Additionally, it is necessary to separate ASO from the sulfone in order to reclaim the sulfone for reuse as a catalyst in the alkylation process.

SUMMARY OF THE INVENTION

It is, therefore, an object of this invention to provide a novel process for the regeneration of alkylation catalysts.

A further object of this invention is to provide a process for the removal of ASO from a mixture containing a sulfone component.

Thus, the process of the present invention relates to the removal of acid soluble oil (ASO) from a mixture containing a sulfone component and ASO by contacting with the mixture a hydrocarbon in an amount that is effective for removing at least a portion of the ASO contained in the mixture and to form an ASO-containing hydrocarbon phase and a sulfone-containing phase.

BRIEF DESCRIPTION OF THE DRAWING

In the accompanying drawings:

FIG, 1 provides schematic representation of the process which is one embodiment of the invention; and FIG, 2 is a graphical representation of the multiple regression models for the extraction of two different ASO materials with alkylate from a sulfolane, ASO and HF mixture as a function of the alkylate-to-mixture ratio.

Figure 1:
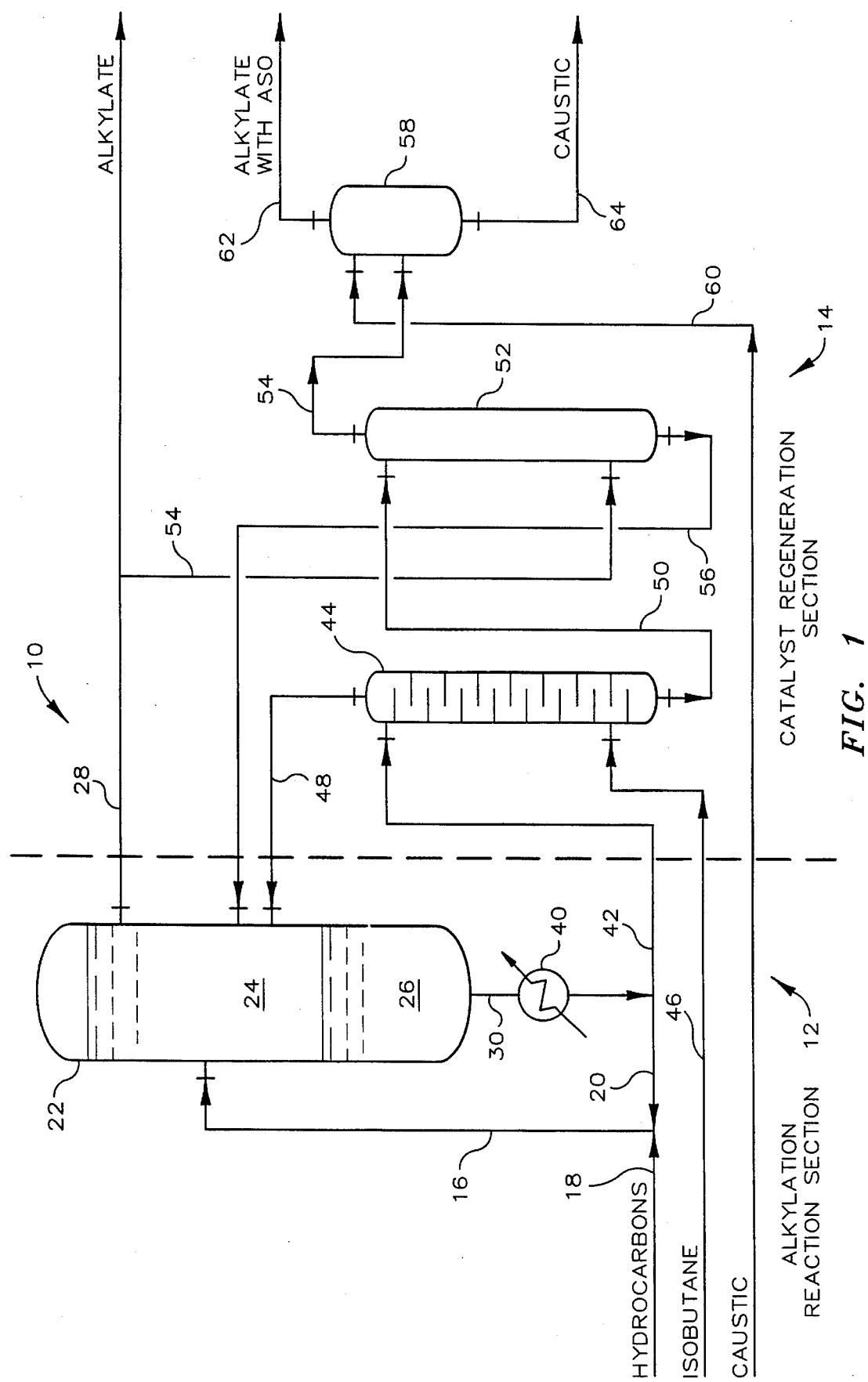

Other objects and advantages of the invention will be apparent from the detailed description of the invention and the appended claims.

DETAILED DESCRIPTION OF THE INVENTION

The acid soluble oil composition referred to herein is produced as a reaction by-product in an alkylation process comprising the step of contacting a hydrocarbon mixture, which comprises olefins and isoparaffins, with an alkylation catalyst, which comprises, consists of, or consists essentially of a hydrogen halide component and a sulfone component. As referred to within this description and in the claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150–160, Volume 8, Number 1, by Miron and Lee. This article is incorporated herein by reference. The physical properties of ASO depend upon the particular hydrocarbon feed processed, the catalyst utilized in the process, feed contaminants such as hydrogen sulfide, butadiene, oxyginates and other compounds, and the alkylation process reaction conditions. Thus, as the term is more narrowly defined herein, ASO will be those conjunct polymers produced as a by-product in the catalyzed reaction of mono-olefins with isoparaffins utilizing a catalyst mixture comprising, consisting of, or consisting essentially of a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane, and the preferred hydrogen halide component is hydrogen fluoride.

The ASO by-product derived from the hydrocarbon reaction catalyzed by a sulfone-containing alkylation catalyst can further be generally characterized as having a specific gravity, with water at 60° F. as the reference, in the range of from about 0.8 to about 1.0, an average molecular weight in the range of from about 250 to about 350, and a bromine number in the range of from about 50 to about 350.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water. In a catalyst composition including hydrogen fluoride and sulfolane, the amount of water present in no event can be more than about 30 weight percent of the total weight of the hydrogen fluoride component, which includes the water. Preferably, the amount of water present in the hydrogen fluoride component is less than about 10 weight percent. Most preferably, the amount of water present in the hydrogen fluoride component is less than 7 weight percent. When referring herein to the hydrogen halide component, or more specifically to the hydrogen fluoride component, of the catalyst composition of the invention, it should be understood that these terms mean that the hydrogen halide component is either an anhydrous mixture of a non-anhydrous mixture. The references herein to weight percent water contained in the hydrogen halide component means the ratio of the weight of water to the sum weight of the water and hydrogen halide multiplied by a factor of 100 to place the weight ratio in terms of percent.

The sulfones suitable for use in this invention are the sulfones of the general formula

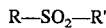

R—SO$_2$—R' wherein R and R' are monovalent hydrocarbon alkyl or aryl substituents, each containing from 1 to 8 carbon atoms, Examples of such substituents include dimethylsulfone, di-n-propylsulfone, diphenylsulfone, ethylmethylsulfone and the alicyclic sulfones wherein the SO$_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

The alkylation catalyst used in the alkylation process wherein an ASO reaction by-product is produced can comprise, consist of, or consist essentially of a hydrogen halide component as described herein and a sulfone component as described herein. Preferably, the ASO by-product will be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with weight ratio of hydrogen fluoride to sulfolane in the alkylation catalyst in the range of from about 1:1 to about 40:1. A preferred weight ratio of hydrogen fluoride to sulfolane can range from about 2.3:1 to about 19:1; and, more preferably, it can range from 3:1 to 9:1.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio, in an alkylation reaction, the better the resultant alkylate quality. present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the give range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the the alkylation zone. Preferably, the contact time is in the range from about 0.05 minute to about 60 minutes. In the alkylation process of the present invention, employing iso-paraffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr) and allowing essentially complete conversion of olefin reactant in the alkylation zone.

The alkylation process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. As described herein, a portion of the catalyst can be continuously regenerated or reactivated by any suitable treatment and returned to the alkylation reactor.

The invention includes a process for removing ASO from a mixture containing a sulfone compound and a concentration of ASO. Generally, the sulfone-containing mixture is in the form of a single liquid phase which comprises a sulfone component and ASO. The process includes the step of contacting or mixing with the sulfone-containing mixture a hydrocarbon or hydrocarbon solvent suitable for removing from the sulfone-containing mixture at least a portion of the ASO contained in such sulfone-containing mixture. The hydrocarbon solvent suitable for removing at least a portion of the ASO contained in the sulfone-containing mixture preferably includes paraffin hydrocarbons having from 4 to 12 carbon atoms. The most preferred hydrocarbon solvents, however, are those produced from the alkylation reaction of isoparaffins and olefins described elsewhere herein as an alkylate or alkylate reaction product or alkylate product.

Any means or method can be used which suitably provides for the mixing or contacting of the solvent hydrocarbon with the sulfone-containing mixture so as to extract or remove from such sulfone-containing mixture at least a portion of the ASO contained therein. Many extraction apparatuses and techniques are known in the art of liquid-liquid extraction summaries of which can be found in *Perry's Chemical Engineers' Handbook, Sixth Edition* published by McGraw-Hill, Inc., 1984, at Section 15 pages 1–20 and Section 21 pages 55–83 and which is incorporated herein by reference. Suitable contacting means can include, for example, mixer-settlers, packed towers, plate-type towers or any other suitable means.

Any amount of the hydrocarbon solvent relative to the quantity of sulfone-containing mixture can be utilized in the process provided that the amount of hydrocarbon solvent is sufficient to remove at least a portion of the ASO dissolved in the sulfone-containing mixture. Generally, the at least a portion of ASO removed is in the range of from about 1 to about 90 weight percent of the ASO contained in the sulfone-containing mixture. For the most efficient process operation, it is preferable to extract as much ASO from the sulfone-containing mixture as is possible for a given ratio of hydrocarbon solvent to sulfone-containing mixture which is preferably at least about 5 weight percent and most preferably at least 10 weight percent.

As earlier indicated, control of the volumetric ratio of hydrocarbon solvent to sulfone-containing mixture is important; because, generally, it impacts the amount of ASO that is extracted from the sulfone-containing mixture with the correlation being that the greater the ratio the higher the percentage of ASO that is removed from the sulfone-containing mixture. Thus, it is desirable for the volumetric ratio of hydrocarbon solvent to sulfone-containing mixture to range from about 0.1:1 to about 10:1. Preferably, the volumetric ratio of hydrocarbon solvent to sulfone-containing mixture is about 0.25:1 to about 5:1, most preferably, the volumetric ratio is in the range of from 0.5:1 to 4:1.

The process conditions under which the hydrocarbon solvent and sulfone-containing mixture can be mixed or contacted include mixing or contacting temperatures in the range of from about 0° F. to about 300° F., with 40° F. to 260° F. being preferred. The mixing or contacting pressures include those within the range of from about 0.5 atmospheres of absolute pressure to about 30 atmospheres of absolute pressure, with 0.95 atmospheres of absolute pressure to 25 atmospheres of absolute pressure being preferred.

This invention contemplates the resolution of problems associated with the regeneration of sulfone-containing alkylation catalyst mixtures by the removal of at least a portion of the ASO contained within such mixtures. The accumulation of ASO in sulfone-containing alkylation catalysts occurs when an alkylation process continuously reuses its catalyst. In a continuous alkylation process, the ASO reaction by-product will build up in the catalyst until, if not removed, it reaches unacceptable concentration levels that can have negative effects upon the catalyst performance and, ultimately, the alkylation product quality. It is generally desirable to maintain the concentration of ASO in the sulfone-containing alkylation catalyst at no more than about 20 weight percent of the catalyst with the weight percent ASO being based upon the total weight of the catalyst mixture exclusive of the ASO component. Preferably, the concentration of the ASO in the sulfone-containing alkylation catalyst is less than about 15 weight percent, and most preferably, the concentration of ASO is less than 10 weight percent. There may be some process advantages in maintaining a low concentration of ASO in the sulfone-containing catalyst mixture, but it is believed that an ASO concentration exceeding about 10 weight percent of the catalyst will have a detrimental effect upon the catalyst performance. Thus, in order to maintain the catalytic activity of a sulfone-containing alkylation catalyst mixture, the catalyst must be processed to remove at least a portion of the ASO contained within such catalyst mixture.

It is desirable, however, for the hydrogen halide component of the ASO contaminated sulfone-containing alkylation catalyst mixture to be minimized before mixing or contacting the resultant sulfone-containing mixture with the hydrocarbon solvent to extract or remove ASO from the sulfone-containing mixture. In particular, when a significant portion of the sulfone-containing alkylation catalyst mixture comprises hydrogen halide; for instance, when the weight ratio of hydrogen halide to sulfolane is in the range of from about 1:1 to about 40:1, it is preferable for a major portion of the hydrogen halide to be removed from the catalyst mixture to give the sulfone-containing mixture or a recovered catalyst mixture. This sulfone-containing mixture of recovered catalyst mixture can comprise, consist of, or consist essentially of a sulfone component, a hydrogen halide component, and ASO. Generally, the concentration of the hydrogen halide component in the recovered catalyst mixture will be less than about 10 weight percent of the catalyst mixture with the weight percent determined by the weight fraction of the hydrogen halide to total weight of hydrogen halide and sulfone multiplied by a factor of 100 to yield a percent. Because it is very difficult to remove the entire amount of hydrogen halide from the catalyst mixture, the lower limit of hydrogen halide concentration can approach about 1.0 weight percent, but, preferably, the lower concentration limit of hydrogen halide can be less than 0.1 weight percent. Thus, the concentration range of hydrogen halide in the recovered catalyst mixture can range from about 0.1 weight percent to about 10 weight percent. Preferably, however, the concentration can range from about 0.1 to about 7.5 weight percent, and most preferably, it can range from 0.1 to 5.0 weight percent.

Now referring to FIG. 1, there is depicted by schematic representation a process 10 which includes an alkylation reaction section 12 and a catalyst regeneration section 14. A hydrocarbon feed mixture, comprising olefins and isoparaffins, is introduced into riser-reactor 16 through conduit 18. Riser-reactor 16 defines a reaction zone wherein the hydrocarbon feed mixture is contacted, or admixed, with a sulfone-containing alkylation catalyst, which comprises sulfolane and hydrogen fluoride, to thereby produce an alkylation reaction mixture comprising an alkylate product, ASO and the sulfone-containing alkylation catalyst. The olefins of the hydrocarbon feed mixture generally comprise one or more olefins having from three to five carbon atoms, and the isoparaffins of the hydrocarbon feed mixture generally will have from four to six carbon atoms. The sulfone-containing alkylation catalyst is introduced into riser-reactor 16 via conduit 20. The admixture of hydrocarbon feed mixture and sulfone-containing alkylation catalyst passes through the reaction zone defined by riser-reactor 16 wherein a reaction takes place in which the olefins of the hydrocarbon feed mixture react with isoparaffins of the hydrocarbon feed mixture to produce the alkylate product. Also, within the reaction zone, the reaction by-product, ASO, is formed. The alkylation reaction mixture, or reaction effluent, from riser-reactor 16 passes to settler vessel 22, which defines a separation zone for separating the alkylate product form the alkylation reaction mixture to produce a separated reaction product 24 and a separated sulfone-containing alkylation catalyst 26. The separated sulfone-containing alkylation catalyst will contain a substantial amount, or that amount that is not soluble in the separated reaction product, of the alkylation reaction by-product, ASO. The separated reaction product 24 passes downstream via conduit 28.

The separated sulfone-containing alkylation catalyst 26 can be recycled via conduits 30 and 20 to riser-rector 16 for reuse as the sulfone-containing alkylation catalyst. Interposed in conduit 30 is catalyst cooler 40, which defines a heat transfer zone for exchanging heat from separated sulfone-containing alkylation catalyst 26 to a heat transfer fluid such as water.

At least a portion, sometimes referred to as a slip stream or a drag stream, of the separated sulfone-containing alkylation catalyst 26 passes by way of conduit 42 to stripping column 44, which defines a separation zone for separating the slip stream of separated sulfone-containing alkylation catalyst into an overhead stream, or hydrogen fluoride stream, comprising a major portion of the hydrogen fluoride contained in the slip stream, and a bottoms stream, comprising a major portion of the sulfone component of the slip stream. The bottoms stream will also contain a major portion of the reaction by-product, ASO, contained in the slip stream. Introduced by way of conduit 46 is vaporous isobutane for stripping the hydrogen fluoride form the slip stream. The overhead stream passes by way of conduit 48 to settler vessel 22 wherein substantially all of hydrogen fluoride is recombined for reuse with the separated sulfone-containing alkylation catalyst 26, and substantially all of the stripping isobutane is combined with the separated reaction product 24.

The bottoms stream from stripping column 44 passes by way of conduit 50 to contacting means 52, which defines a contacting zone, or alternatively, a mixing zone, for contacting or mixing, or both, the bottoms stream with a hydrocarbon or an alkylate hydrocarbon product. A portion of the separated reaction product passing through conduit 28 passes by way of conduit 54 to contacting means 52 wherein the portion of separated reaction product is contacted with the bottoms stream to thereby remove from the bottoms stream a portion of the ASO contained therein. An ASO-containing hydrocarbon phase passes from contacting means 52 by way of conduit 54 and a sulfone-containing phase passes from contacting means 52 by way of conduit 56 to settler vessel 22 wherein it is combined with the separated sulfone-containing alkylation catalyst.

The ASO-containing hydrocarbon phase is passed to contacting vessel 58, which defines a contacting zone for contacting the ASO-containing hydrocarbon phase with a caustic material to thereby neutralize and/or remove the hydrofluoride contained in the ASO-containing hydrocarbon phase. The caustic is introduced into contacting vessel 58 by way of conduit 60. The neutralized ASO-containing hydrocarbon phase passes from contacting vessel 58 via conduit 62 and spent caustic passes from contacting vessel 58 via conduit 64.

The following example demonstrates the advantages of the present invention. The example is by way of illustration only, and is not intended as limitations upon the invention as set out in the appended claims.

Example

Two designed extraction experiments, shown in Tables I and II, explored the efficiency of ASO extraction from simulated rerun tower bottoms, i.e. mixture of sulfolane, hydrogen fluoride, ASO, by light alkylate obtained from Phillips Petroleum Company, Borger, Tex. refinery over the range of HF concentrations from 1 to 12 weight percent, and alkylate-to-simulated return tower bottoms ratios of from 1/3 to 3/1 by volume. The ASO used for the Table I experiment was obtained from Phillips Petroleum Company, Borger, Tex. refinery, and the ASO used for the Table II experiment was obtained from Phillips Petroleum Company, Sweeny, Tex. refinery.

Each experiment was a two-level factorial experiment using two replicates of the center point. Run order was randomized to reduce systematic error. The total volumes were adjusted to equal 200 mL in each case for convenience of experimentation in the lab. The stock solution mentioned in Tables I and II was 15% HF in sulfolane; HF was added in this manner for convenience and accuracy, as better accuracy could be obtained than by adding HF gas. Each standard simulated rerun bottoms contained 9/1 sulfolane/ASO by weight, plus the indicated weight percent of HF.

All components were added to one 250 mL Teflon separatory funnel, shaken, and allowed to separate into phases. The phases were taken off, and the amount of ASO in the top (alkylate) and bottoms (sulfolane) phases determined by UV-VIS analysis at 460 nm, using standard curves made from the ASO being analyzed in either alkylate or sulfolane. It was observed that the phases were without exception quite acidic, so the standard dilution samples included 2% HF.

Summaries of the results of the experiments are given in

Figure 2:
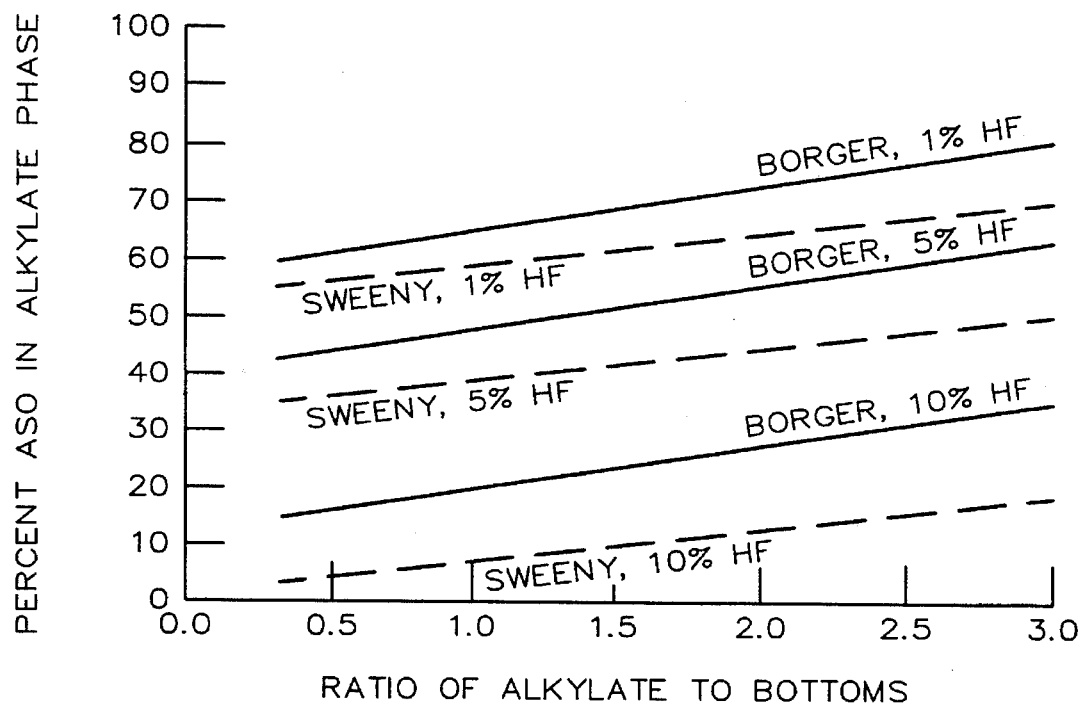

Tables III and IV. These data were analyzed using the program CSS Statistica, Release 3.1, StarSoft, Tulsa, Okla., 1992. All points were used in analysis of the results. Multiple regression models were developed for the ASO material obtained from Borger and Sweeny and are depicted in FIG. 2. The data presented herein demonstrate that alkylate can suitably be used as an extractant for removing ASO from sulfolane. As can clearly be observed from the data presented in FIG. 2, the extraction efficiency improves or increases with an increasing ratio of alkylate-to-simulated rerun bottoms. Also, the efficiency of the extraction decreases with an increasing concentration of hydrogen fluoride in the simulated rerun tower bottoms. Therefore, there is a critical level of hydrogen fluoride that may be present in the simulated rerun tower bottoms above which alkylate is ineffective as an extractant. Furthermore, because of the difference in extraction efficiencies for the two types of ASO, it appears that the character of the ASO can have an influence on such extraction efficiency.

TABLE I

Designed Experiment for Borger ASO

| Run | HF | Ratio | wt. % HF | ratio alky/ mix | mL stock | mL sulf | g ASO | mL alky |
|---|---|---|---|---|---|---|---|---|
| 1 | 0 | 0 | 6.5 | 1.00 | 33.52 | 57.09 | 8.84 | 100 |
| 2 | 1 | 1 | 12.0 | 3.00 | 29.42 | 16.12 | 4.20 | 150 |
| 3 | 1 | −1 | 12.0 | 0.33 | 88.26 | 48.35 | 12.61 | 50 |
| 4 | −1 | −1 | 1.0 | 0.33 | 8.16 | 126.99 | 13.99 | 50 |
| 5 | 0 | 0 | 6.5 | 1.00 | 33.52 | 57.09 | 8.84 | 100 |
| 6 | −1 | 1 | 1.0 | 3.00 | 2.72 | 42.33 | 4.66 | 150 |

TABLE II

Designed Experiment for Sweeny ASO

| Run | HF | Ratio | wt. % HF | ratio alky/ mix | mL stock | mL sulf | g ASO | mL alky |
|---|---|---|---|---|---|---|---|---|
| 1 | 0 | 0 | 6.5 | 1.00 | 33.52 | 57.09 | 8.63 | 100 |
| 2 | 1 | 1 | 12.0 | 3.00 | 29.42 | 16.12 | 4.10 | 150 |
| 3 | 1 | −1 | 12.0 | 0.33 | 88.26 | 48.35 | 12.31 | 50 |
| 4 | −1 | −1 | 1.0 | 0.33 | 8.16 | 126.99 | 13.65 | 50 |
| 5 | 0 | 0 | 6.5 | 1.00 | 33.52 | 57.09 | 8.63 | 100 |
| 6 | −1 | 1 | 1.0 | 3.00 | 2.72 | 42.33 | 4.55 | 150 |

TABLE III

Results of Borger Designed Experiment

| Run | T/B | mL Total | ASO g/100 mL | ASO, g Total | % of Total ASO |
|---|---|---|---|---|---|
| 1 | T | 93.6 | 2.78 | 2.60 | 36.63 |
| 1 | B | 91.9 | 4.89 | 4.49 | — |
| 2 | T | 142.0 | 0.65 | 0.92 | 33.71 |
| 2 | B | 46.0 | 3.93 | 1.81 | — |
| 3 | T | 63.4 | 1.02 | 0.65 | 1.44 |
| 3 | B | 221.9 | 20.02 | 44.42 | — |
| 4 | T | 45.7 | 19.16 | 8.76 | 69.05 |
| 4 | B | 150.9 | 2.6 | 3.92 | — |
| 5 | T | 78.0 | 2.94 | 2.29 | 36.58 |
| 5 | B | 95.2 | 4.18 | 3.98 | — |
| 6 | T | 139.6 | 1.09 | 1.52 | 77.31 |
| 6 | B | 50.8 | 0.88 | 0.45 | — |

TABLE IV

Results of Sweeny Designed Experiment

| Run | T/B | mL Total | ASO g/100 mL | ASO, g Total | % of Total ASO |
|---|---|---|---|---|---|
| 1 | T | 106 | 0.95 | 1.01 | 15.48 |
| 1 | B | 93 | 5.91 | 5.50 | — |
| 2 | T | 154 | 0.27 | 0.42 | 10.48 |
| 2 | B | 46 | 7.73 | 3.56 | — |
| 3 | T | 46 | 1.02 | 0.47 | 2.88 |
| 3 | B | 144 | 11.03 | 15.89 | — |
| 4 | T | 63 | 2.86 | 1.80 | 59.42 |
| 4 | B | 137 | 0.90 | 1.23 | — |
| 5 | T | 106 | 0.80 | 0.85 | 17.73 |
| 5 | B | 94 | 4.20 | 3.95 | — |
| 6 | T | 104 | 0.28 | 0.29 | 80.68 |
| 6 | B | 46 | 0.15 | 0.07 | — |

Reasonable variations and modifications are possible within the scope of this disclosure without departing from the scope and spirit thereof.

That which is claimed is:

1. A process for removing acid soluble oil (ASO) from a sulfone-containing mixture containing a sulfone component and ASO, said process comprising the step of:

contacting with said sulfone-containing mixture a hydrocarbon in an amount sufficient to remove from said sulfone-containing mixture at least a portion of the ASO contained therein and to thereby form an ASO containing hydrocarbon phase and a sulfone-containing phase.

2. A process as recited in claim 1 wherein said amount of said hydrocarbon contacted with said sulfone-containing mixture is such that the volumetric ratio of said hydrocarbon to said sulfone-containing mixture is in the range of from about 0.1:1 to about 10:1.

3. A process as recited in claim 2 wherein said at least a portion is in the range of from 1 to 90 percent of the ASO contained in said sulfone-containing mixture.

4. A process as recited in claim 3 wherein said sulfone component is sulfolane and is present in said sulfone-containing mixture at a concentration in the range of from at least a portion upwardly to about 90 weight percent and the ASO concentration in said sulfone-containing mixture is in the range of from at least a portion upwardly to about 10 weight percent.

5. A process for removing acid soluble oil (ASO) from a sulfone-containing mixture, comprising a sulfone component and ASO, said process comprising the step of:

contacting with said sulfone-containing mixture a hydrocarbon, comprising an alkylate produced by the catalytic alkylation of olefins by isoparaffins, in an amount such that the volumetric ratio of said hydrocarbon to said sulfone-containing mixture is in the range of from about 0.25:1 to about 5:1 to thereby extract from said sulfone-containing mixture at least a portion of the ASO contained therein; and forming two immiscible phases including an ASO-containing hydrocarbon phase, comprising said hydrocarbon and having therein ASO extracted from said sulfone-containing mixture, and a sulfone-containing phase, comprising sulfone.

6. A process as recited in claim 5 wherein said sulfone component is sulfolane and is present in said sulfone-containing mixture at a concentration in the range of from at least a portion upwardly to about 90 weight percent and the ASO concentration in said sulfone-containing mixture is in the range of from at least a portion upwardly to about 25 weight percent.

7. A process as recited in claim 6 wherein said at least a portion is in the range of from about 1 to about 90 percent of the ASO contained in said sulfone-containing mixture.

8. A process, comprising: contacting a sulfone-containing mixture, comprising a sulfone and an acid soluble oil (ASO), with a hydrocarbon; and then, forming two immiscible phases including a hydrocarbon with ASO phase and a sulfone phase, wherein said hydrocarbon with ASO phase, comprises ASO, and said sulfone phase, comprises sulfone.

9. A process as recited in claim 8 wherein the amount of said hydrocarbon contacted with said sulfone-containing mixture is such that the volumetric ratio of said hydrocarbon to said sulfone-containing mixture is in the range of from 0.1:1 to 10:1.

10. A process as recited in claim 9 wherein the concentration of ASO in said hydrocarbon with ASO phase is in the range of from at least a portion upwardly to about 10 weight percent.

11. A process as recited in claim 10 wherein said sulfone is sulfolane and the concentration of sulfone in said sulfone phase is in the range of from at least a portion upwardly to about 90 weight percent.

\* \* \* \* \*